(12) United States Patent
Dehestani

(10) Patent No.: US 11,767,306 B2
(45) Date of Patent: Sep. 26, 2023

(54) METHODS FOR CONVERTING CBD TO TETRAHYDROCANNABINOLS

(71) Applicant: Cannacraft, Inc., Santa Rosa, CA (US)

(72) Inventor: Ahmad Dehestani, Walnut Creek, CA (US)

(73) Assignee: Cannacraft, Inc, Santa Rosa, CA (US)

( * ) Notice: Subject to any disclaimer, the term of this patent is extended or adjusted under 35 U.S.C. 154(b) by 107 days.

(21) Appl. No.: 17/076,052

(22) Filed: Oct. 21, 2020

(65) Prior Publication Data

US 2021/0221783 A1 Jul. 22, 2021

Related U.S. Application Data

(60) Provisional application No. 62/962,545, filed on Jan. 17, 2020.

(51) Int. Cl.
*C07D 311/80* (2006.01)
*B01D 15/32* (2006.01)
*B01D 15/16* (2006.01)
*B01J 31/14* (2006.01)

(52) U.S. Cl.
CPC .......... *C07D 311/80* (2013.01); *B01D 15/163* (2013.01); *B01D 15/325* (2013.01); *B01J 31/143* (2013.01)

(58) Field of Classification Search
CPC .................................................. C07D 311/80
See application file for complete search history.

(56) References Cited

U.S. PATENT DOCUMENTS

| 4,877,530 A | 10/1989 | Moses |
| 8,481,085 B2 | 7/2013 | Musty |
| 11,000,818 B1 | 5/2021 | Sanchez |
| 2004/0143126 A1* | 7/2004 | Webster ............... C07D 311/80 549/390 |
| 2006/0257463 A1 | 11/2006 | Elsohly |
| 2007/0010700 A1 | 1/2007 | Bensmann |
| 2007/0093665 A1* | 4/2007 | Burdick .................. C07C 29/00 549/390 |
| 2015/0297654 A1 | 10/2015 | Speier |
| 2017/0008870 A1 | 1/2017 | Dibble |
| 2018/0056211 A1 | 3/2018 | Seabrook |
| 2018/0085308 A1 | 3/2018 | Renwick |
| 2018/0147247 A1 | 5/2018 | Ivanov |
| 2018/0193403 A1 | 7/2018 | George |
| 2019/0153484 A1 | 5/2019 | Bray |
| 2019/0240593 A1 | 8/2019 | Murphy |
| 2020/0054962 A1 | 2/2020 | Vanaman |
| 2020/0172503 A1 | 6/2020 | Oroskar |
| 2020/0215137 A1 | 7/2020 | Speier |
| 2021/0236955 A1 | 8/2021 | Dehestani |
| 2021/0275618 A1 | 9/2021 | Davidson |

FOREIGN PATENT DOCUMENTS

| CA | 2455129 C | 10/2013 | |
| CN | 104011218 A | 8/2014 | |
| DE | 10106024 A1 * | 8/2002 | ........... C07D 311/80 |
| WO | 2017184642 A1 | 10/2017 | |

OTHER PUBLICATIONS

Hazekamp, A. Med. Cannabis Cannabinoids 2018, 65-72 (Year: 2018).*
English Translation of Raman patent publication CN 104011216A, Aug. 27, 2014. (Year: 2014).

* cited by examiner

*Primary Examiner* — Matthew P Coughlin
(74) *Attorney, Agent, or Firm* — Innovation Law LLP

(57) ABSTRACT

This disclosure provides a method for converting CBD to a tetrahydrocannabinol featuring the use of cheap and non-toxic aluminum isopropoxide as a catalyst. The method comprises (a) providing a reaction mixture comprising a catalyst in an organic solvent, wherein the catalyst comprises aluminum isopropoxide; (b) adding a reagent comprising CBD to the reaction mixture; (c) mixing the reaction mixture and allowing a reaction for converting CBD to a tetrahydrocannabinol to occur for a predetermine period of time; (d) removing the catalyst by filtration upon the completion of the reaction; (e) removing the organic solvent; and (f) eluting the tetrahydrocannabinol from the organic phase.

19 Claims, 2 Drawing Sheets

Sample Name      : Delta-8 test 2
Sample ID        : H1281
Data Filename    : H1281_Delta-8 test 2_6112019_03.lcd
Method Filename  : DJA 45 C 10 min iso 75b calibrated SLW1.lcm
Batch Filename   : 190611_AM2.lcb
Vial #           : 2-34                              Sample Type    : Unknown
Injection Volume : 1 uL
Date Acquired    : 6/11/2019 4:34:17 PM              Acquired by    : System Administrator
Date Processed   : 6/11/2019 4:44:18 PM              Processed by   : System Administrator
Sample Amount    : 0.101
Dilution         : 20

<Quantitative Results>

PDA

| ID# | Name | Ret. Time | Area | Conc. | Unit |
|---|---|---|---|---|---|
| 1 | CBDA | -- | -- | -- | % |
| 2 | CBGA | -- | -- | -- | % |
| 3 | CBG | 4.031 | 1659 | 0.094 | % |
| 4 | CBD | -- | -- | -- | % |
| 5 | THCV | 4.436 | 4309 | 0.265 | % |
| 6 | CBN | 5.697 | 3473 | 0.132 | % |
| 7 | THC9 | 7.003 | 211477 | 13.839 | % |
| 8 | THC8 | 7.239 | 929683 | 67.938 | % |
| 9 | $\Delta^{10}$-THC | 8.292 | 40929 | 2.050 | % |
| 10 | THCA | 8.767 | 4265 | 0.221 | % |
| Total | | | | 84.538 | |

FIG. 1

```
Sample Name     : Delta-8 part II
Sample ID       : H1366
Data Filename   : H1366_Delta-8 part II_6132019_01.lcd
Method Filename : DJA 45 C 10 min iso 75b calibrated 4WD.lcm
Batch Filename  : 190613_AM2.lcb
Vial #          : 1-38                          Sample Type    : Unknown
Injection Volume: 1 uL
Date Acquired   : 6/13/2019 4:46:47 PM          Acquired by    : System Administrator
Date Processed  : 6/14/2019 9:58:40 AM          Processed by   : System Administrator
Sample Amount   : 0.09
Dilution        : 20
```

<Quantitative Results>

| PDA ID# | Name | Ret. Time | Area | Conc. | Unit |
|---|---|---|---|---|---|
| 1 | CBDA | -- | -- | -- | % |
| 2 | CBGA | -- | -- | -- | % |
| 3 | CBG | 3.940 | 3100 | 0.219 | % |
| 4 | CBD | -- | -- | -- | % |
| 5 | THCV | 4.493 | 13851 | 0.946 | % |
| 6 | CBN | 5.633 | 3437 | 0.135 | % |
| 7 | THC9 | 6.941 | 73679 | 5.368 | % |
| 8 | THC8 | 7.176 | 930083 | 75.801 | % |
| 9 | $\Delta^{10}$-THC | 8.459 | 20075 | 1.149 | % |
| 10 | THCA | 8.723 | 11985 | 0.737 | % |
| Total | | | | 84.155 | |

FIG. 2

METHODS FOR CONVERTING CBD TO TETRAHYDROCANNABINOLS

CROSS-REFERENCE TO RELATED APPLICATIONS

This application claims priority under 35 U.S.C. § 119(e) to U.S. Provisional patent Application No. 62/962,545, filed Jan. 17, 2020. The foregoing applications are incorporated by reference herein in its entirety.

FIELD OF THE INVENTION

This disclosure relates generally to methods for converting CBD to tetrahydrocannabinol and more specifically to methods for converting CBD to tetrahydrocannabinol by using aluminum isopropoxide as a catalyst.

BACKGROUND OF THE INVENTION

Cannabinoids are a group of compounds that are ligands to cannabinoid receptors ($CB_1$, $CB_2$) found in the human body (Pertwee, 1997). Cannabinoids were originally found from *Cannabis sativa* L., an origin of marijuana and hashish. Over the last few years, public interest in Cannabis as medicine has been growing, based in no small part on the fact that Cannabis has long been considered to have medicinal properties, ranging from treatment of cramps, migraines, convulsions, appetite stimulation and attenuation of nausea and vomiting. Advocates of medical marijuana suggest that components of Cannabis can be useful for glaucoma, Parkinson's disease, Huntington's disease, migraines, epilepsy, and Alzheimer's disease.

Marijuana refers to varieties of Cannabis having a high content of $\Delta^9$-tetrahydrocannabinol ($\Delta^9$-THC), which is the psychoactive ingredient of marijuana whereas industrial hemp refers to varieties of the Cannabis plant that have a low content of $\Delta^9$-THC. Furthermore, $\Delta^9$-THC is only one of a family of about 60 bi- and tri-cyclic compounds named cannabinoids. For example, $\Delta^8$-THC is a double bond isomer of $\Delta^9$-THC and is a minor constituent of most varieties of Cannabis (Hollister and Gillespie, 1972, *Clin Pharmacol Ther* 14: 353).

Gaoni et al. described methods of converting CBD to $\Delta^8$-THC and $\Delta^9$-THC in the presence of ethanol and HCL (1966, *Tetrahedron* 22: 1481-1488). The solution was then poured into water and extracted with ether. The ether solution was washed with water, dried ($Na_2SO_4$), and evaporated. $\Delta^8$-THC and $\Delta^9$-THC were eluted from the resulting oil and separated by chromatography. In another method, CBD was dissolved in benzene containing p-toluene sulphonic acid. The reaction mixture was poured into water, and the upper layer was separated, washed with $NaHCO_3$, and dried. Elution with pentane-ether gave an oily material which was subsequently distilled. The crude oil product was purified by vacuum distillation, although the purity of the resulting THC was not provided.

Given the potential medicinal value of cannabinoid, there remains a strong need for improved methods of converting CBD to tetrahydrocannabinol (e.g., $\Delta^9$-THC, $\Delta^8$-THC).

BRIEF DESCRIPTION OF THE DRAWINGS

FIG. 1 shows the exemplary results from a quantitative analysis of the products from the conversion reactions.

FIG. 2 shows the exemplary results from another quantitative analysis of the products from the conversion reactions.

SUMMARY OF THE INVENTION

This disclosure addresses the need mentioned above in a number of aspects. In one aspect, this disclosure provides a method for converting CBD to tetrahydrocannabinol. The method comprises (a) providing a reaction mixture comprising a catalyst in an organic solvent, wherein the catalyst comprises aluminum isopropoxide; (b) adding a reagent comprising CBD to the reaction mixture; (c) mixing the reaction mixture and allowing a reaction for converting CBD to tetrahydrocannabinol to occur for a predetermined period of time; (d) removing the catalyst by filtration upon the completion of the reaction; (e) removing the organic solvent; and (f) eluting the tetrahydrocannabinol from the organic phase.

In some embodiments, the tetrahydrocannabinol is $\Delta^8$-tetrahydrocannabinol ($\Delta^8$-THC). In some embodiments, the tetrahydrocannabinol is $\Delta^9$-tetrahydrocannabinol ($\Delta^9$-THC).

In some embodiments, the yield of the tetrahydrocannabinol is at least 60% (e.g., at least 65%, at least 70%, at least 75%, at least 80%, at least 85%, at least 90%, at least 95%, at least 98%, at least 99%).

In some embodiments, the ratio of $\Delta$8-THC to $\Delta^9$-THC is between about 1:10 and about 10:1 (e.g., between about 1:5 and about 10:1, between about 1:3 and about 10:1, between about 1:1 and about 10:1, between about 1:1 and about 6:1, between about 1:1 and about 5:1, between about 2:1 and about 10:1, between about 2:1 and about 8:1, between about 2:1 and about 6:1, between about 2:1 and about 5:1).

In some embodiments, the method comprises, following mixing the reaction mixture, heating the reaction mixture to a temperature between about 70° C. and about 110° C. to allow complete mixing. In some embodiments, the method comprises, following mixing the reaction mixture, the reaction mixture is heated to about 90° C. to allow complete mixing. In some embodiments, heating is stopped when the reaction mixture is substantially mixed.

In some embodiments, the organic solvent comprises isopropyl.

In some embodiments, removing the organic solvent is performed under a pressure near atmospheric pressure to a pressure substantially below atmospheric pressure.

In some embodiments, mixing the reaction mixture is performed a nitrogen atmosphere.

In some embodiments, eluting the tetrahydrocannabinol on an HPLC column or an RP-HPLC column. In some embodiments, the tetrahydrocannabinol is eluted with water-methanol or water-acetonitrile.

In some embodiments, the reagent further comprises tetrahydrocannabinol, such as $\Delta$9-THC.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

DETAILED DESCRIPTION OF THE INVENTION

Described herein are methods and protocols for converting cannabidiol (CBD) to $\Delta^8$-tetrahydrocannabinol ($\Delta^8$-THC) or $\Delta^9$-tetrahydrocannabinol ($\Delta^9$-THC) or $\Delta$10-THC. The methods and protocols feature the use of aluminum isopropoxide to catalyze the conversion. Compared to the existing methods described in the literature using toxic and expensive reagents, the present method uses aluminum isopropoxide as a catalyst that is a non-toxic and low-cost reagent. Importantly, aluminum isopropoxide is in a solid form and thus can be readily removed by filtration after the reaction is completed.

A. METHOD FOR CONVERTING CBD TO A TETRAHYDROCANNABINOL

In one aspect, this disclosure provides a method for converting CBD to tetrahydrocannabinol. The method comprises (a) providing a reaction mixture comprising a catalyst in an organic solvent, wherein the catalyst comprises aluminum isopropoxide; (b) adding a reagent comprising CBD to the reaction mixture; (c) mixing the reaction mixture and allowing a reaction for converting CBD to tetrahydrocannabinol to occur for a predetermined period of time; (d) removing the catalyst by filtration upon the completion of the reaction; (e) removing the organic solvent; and (f) eluting the tetrahydrocannabinol from the organic phase.

In some embodiments, the tetrahydrocannabinol is $\Delta^8$-tetrahydrocannabinol ($\Delta$8-THC). In some embodiments, the tetrahydrocannabinol is $\Delta^9$-tetrahydrocannabinol ($\Delta$9-THC).

In some embodiments, the ratio of $\Delta$8-THC to $\Delta$9-THC is between about 1:10 and about 10:1 (e.g., between about 1:5 and about 10:1, between about 1:3 and about 10:1, between about 1:1 and about 10:1, between about 1:1 and about 6:1, between about 1:1 and about 5:1, between about 2:1 and about 10:1, between about 2:1 and about 8:1, between about 2:1 and about 6:1, between about 2:1 and about 5:1).

The major chemical difference between the two compounds is that $\Delta^9$-THC is easily oxidized to cannabinol, whereas $\Delta^8$-THC does not and is, in fact, very stable. $\Delta^8$-THC, for the most part, produces similar psychometric effects as does $\Delta^9$-THC, but is generally considered to be 50% less potent than $\Delta^9$-THC and has been shown in some cases to be 3-10 times less potent. $\Delta^8$-THC has also been shown to be more (200%) effective an anti-emetic than $\Delta^9$-THC and has been used as an anti-emetic in children, based on the belief that the side effects of $\Delta^9$-THC and $\Delta^8$-THC, such as anxiety and dysphoria, are more prevalent in adults than children (Abrahamov et al., 1995, *Life Sciences* 56: 2097-2102. It is of note that CBD is typically about 2% (0.54%) dry weight of hemp chaff, $\Delta^8$-THC is approximately 0.2% (0.05-0.5%) dry weight and $\Delta^9$-THC is approximately 0.1% (0.05-0.3%).

As will be appreciated by one knowledgeable in the art and as discussed below, the reaction times may be varied somewhat, producing products at different yields and purities. In some embodiments, the yield of the tetrahydrocannabinol is at least 60% (e.g., at least 65%, at least 70%, at least 75%, at least 80%, at least 85%, at least 90%, at least 95%, at least 98%, at least 99%).

Generally, the preparation of $\Delta^9$-THC requires the shortest time, with $\Delta^8$-THC being the second and $\Delta^{10}$-THC being the slowest. For example, to obtain $\Delta^9$-THC, less catalyst and reaction time are needed. In one example, $\Delta^9$-THC can be obtained in less than 5 minutes of reaction time at a temperature above 120° C. In another example, $\Delta^8$-THC can be obtained in between 2 and 4 hours of reaction time. In another example, $\Delta^{10}$-THC can be obtained in about 12 hours of reaction time.

Yield can be determined by looking at the peak area for the isolated compound in the gas chromatography-mass spectra analysis of the crude reaction product mixture. It is important to note that in the prior art, the yield is often calculated on the basis of first isolated crude product before final purification. In some embodiments of the process, as discussed below, the yield is at least 50%. In other embodiments, the yield is at least 60%. In other embodiments, the yield is at least 70%. In yet other embodiments, the yield is 70-85%.

Purity can be determined by GC-MS and also by analytical HPLC. The total ion chromatogram from the GC-MS gives information similar to that provided by an FID-GC in that the peak area is proportional to the mass of the analytes detected. Total peak area and the peak areas of the individual analytes can be compared in the GC-MS case as long as the masses are in generally the same range. As discussed below, in some embodiments, the purity of the tetrahydrocannabinol isolated by the process is greater than 90%. In yet other embodiments, purity is greater than 95%. In yet other embodiments, purity is greater than 97%. In yet other embodiments, purity is 90-99%.

In some embodiments, the method comprises, following mixing the reaction mixture, heating the reaction mixture to a temperature between about 70° C. and about 110° C. to allow complete mixing. In some embodiments, the method comprises, following mixing the reaction mixture, the reaction mixture is heated to about 90° C. to allow complete mixing. In some embodiments, heating is stopped when the reaction mixture is substantially mixed.

In some embodiments, the organic solvent comprises isopropyl.

In some embodiments, removing the organic solvent is performed under a pressure near atmospheric pressure to a pressure substantially below atmospheric pressure.

In some embodiments, mixing the reaction mixture is performed a nitrogen atmosphere.

In some embodiments, eluting the tetrahydrocannabinol on an HPLC column or an RP-HPLC column. In some embodiments, the tetrahydrocannabinol is eluted with water-methanol or water-acetonitrile.

In some embodiments, the reagent further comprises tetrahydrocannabinol, such as $\Delta$9-THC.

The tetrahydrocannabinol may then be combined with suitable excipients known in the art, thereby forming a pharmaceutical composition.

B. COMPOSITIONS CONTAINING TETRAHYDROCANNABINOL

In some embodiments, the resulting tetrahydrocannabinol (e.g., $\Delta^9$-THC, $\Delta^8$-THC) at therapeutically effective concentrations or dosages be combined with a pharmaceutically or pharmacologically acceptable carrier, excipient or diluent, either biodegradable or non-biodegradable.

Examples of carriers include, but are by no means limited to, for example, poly(ethylene-vinyl acetate), copolymers of lactic acid and glycolic acid, poly(lactic acid), gelatin, collagen matrices, polysaccharides, poly(D,L lactide), poly(malic acid), poly(caprolactone), celluloses, albumin, starch, casein, dextran, polyesters, ethanol, methacrylate, polyurethane, polyethylene, vinyl polymers, glycols, mixtures thereof and the like. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecyl sulfate, carboxymethylcellulose calcium, carboxymethylcellulose sodium, methylcellulose, hydroxyethylcellulose, hydroxypropyl cellulose, hydroxypropylmethylcellulose phthalate, noncrystalline cellulose, magnesium aluminum silicate, triethanolamine, polyvinyl alcohol, polyvinylpyrrolidone, sugars, and starches. See, for example, Remington: The Science and Practice of Pharmacy, 1995, Gennaro ed.

In some embodiments, the chemicals can be purified and blended together to produce a formulation similar in form to that for Marinol®. In these formulations, the active ingredient is dissolved in sesame seed oil or similar oil and enclosed in a gel-capsule. In other embodiments, the formulation may be arranged to be used as an injectable or as an aerosol. In these embodiments, as will be apparent to one of skill in the art, the appropriate pharmaceutically-acceptable additives may be added so that the pharmaceutical composition is in the appropriate form.

As will be appreciated by one knowledgeable in the art, the formulation may be used as, for example, an anti-emetic, appetite stimulant, or as a treatment for nausea, dementia, Alzheimer's disease, glaucoma, high blood pressure, inflammation or multiple sclerosis. As such, when administered to an individual in need of such treatment, the pharmaceutical composition of $\Delta^8$-THC and CBD will accomplish at least one of the following: reduce nausea, promote or stimulate appetite, reduce vomiting and/or promote a general feeling of well-being.

In some embodiments, the compositions can be used for treatment of a subject afflicted with or suffering from nausea, muscular spasms, multiple sclerosis, uterine cramps, bowel cramps, a movement disorder, pain, migraine headache, glaucoma, asthma, inflammation, insomnia, high blood pressure, cancer, anxiety, convulsions, depression or psychosis.

In use, the pharmaceutical composition is administered to a patient suffering from vomiting or nausea or at risk of developing these symptoms, possibly due to another treatment. As discussed above, $\Delta^8$-THC is a potent anti-emetic but has the side effect of also being psychoactive. However, combining $\Delta^8$-THC with CBD diminishes these psychoactive effects, resulting in an anti-emetic with no or lessened psychoactive side effects.

In some embodiments, the pharmaceutical composition may be combined with other compounds or compositions known in the art such that the pharmaceutical composition is in the form of, for example, a pill, tablet, capsule or liquid form. The pharmaceutical composition may also be arranged to be injected, taken orally as a liquid or be in an aerosol form.

It is of note that the pharmaceutical composition discussed above may be prepared to be administered in a variety of ways, for example, orally or intravenously, using means known in the art and as discussed below. In other embodiments, the pharmaceutical composition may be administered as a patch.

The compositions prepared by the disclosed methods can be an oral dosage composition, a pulmonary or nasal dosage composition, or a topical dosage composition. The compositions can be in the form of a solution, a spray, or a powder. In some embodiments, the composition is in the form of a tablet, a capsule, a jelly, a cream, an ointment, a suspension, a solution, a spray or a chewing gum.

In some embodiments, the pharmaceutical composition at concentrations or dosages discussed herein may be combined with a pharmaceutically or pharmacologically acceptable carrier, binder, excipient or diluent, either biodegradable or non-biodegradable. See, for example, *Remington: The Science and Practice of Pharmacy,* 1995, Gennaro ed.

Additional Ingredients

Cannabinoids are susceptible to oxidation and hydrolysis. Over time it is possible for cannabinoids to be exposed to oxygen, hydrogen ions (acids, water), in addition to any other environmental factors that will cause their degradation.

Organic bases can be used to prevent the degradation of the cannabinoids. These organic bases include, but are not limited to, butyl hydroxyl anisole (BHA), butyl hydroxyl toluene (BHT), and sodium ascorbate; at concentrations between 0.001 to 5%> w/w, for example. Organic bases such as the following can improve the stability of cannabinoids from chemical degradation for up to 2 years: BHA 0.001 to 5% w/w, BHT 0.001 to 5% w/w, and combinations of BHA and BHT can also be used.

Antioxidants can be used to prevent or at least inhibit or mitigate the degradation of cannabinoids from oxidation. Examples of antioxidants include: ethanol, polyethylene glycol 300, polyethylene glycol 400, propylene glycol, propylene carbonate, N-methyl-2-pyrrolidones, dimethylacetamide, dimethyl sulfoxide, hydroxypropyl-P-cyclodextrins, sulfobutylether-β-cyclodextrin, a-cyclodextrin, HSPC phospholipid, DSPG phospholipid, DMPC phospholipid, DMPG phospholipid, ascorbyl palmitate, butylated hydroxyanisole, butylated hydroxyanisole, propyl gallate, a-tocopherol, γ-tocopherol, propyl gallate, lecithin, Vitamin E tocopherol, sesamin, sesamol, sesamolin, alpha-tocopherol, ascorbic acid, ascorbyl palmitate, fumaric acid, malic acid, sodium metabisulfite, and EDTA. Specific antioxidant examples include, but are not limited to: Ascorbic Acid: 0.001 to 5% w/w, Vitamin E Tocopherol: 0.001 to 5% w/w, Tocopherol: 0.001 to 5% w/w, and combinations of ascorbic acid, vitamin E tocopherol, and tocopherol can be used for this invention.

Chelating agents can prevent or at least mitigate the degradation of cannabinoids from metal ions in solution. Chelating agents include, but are not limited to, ethylenediaminetetraacetic acid (EDTA), phosphoric acid, polyphosphates, polysaccharides, citric acid, and any combination thereof.

Preservatives can be used to prevent microbial spoilage. These preservatives include: methylparabens, ethylparabens, propylparabens, butylparabens, sorbic acid, acetic acid, propionic acid, sulfites, nitrites, sodium sorbate, potassium sorbate, calcium sorbate, benzoic acid, sodium benzonatate, potassium benzonatate, calcium benzonatate, sodium metabisulfite, propylene glycol, benzaldehyde, butylated hydroxytoluene, butylated hydroxyanisole, formaldehyde donors, essential oils, citric acid, monoglyceride, phenol, mercury components and any combination thereof. Specific examples include, but are not limited to, sodium benzoate and potassium sorbate.

Additionally, the pH can be lowered to prevent or retard microbial growth. Lowering the pH below 4.0 is sufficiently low enough to prevent microbial growth for a minimum of 1 month.

Preservatives and/or stabilizers can be added during formulation. Depending on the nature of the preservative/stabilizer, it may be contained in either the oil phase, interfacial layer, or the aqueous continuous phase. Once dissolved, the preservatives and stabilizers are released into the solution imparting their properties into the aqueous system. This allows beverage manufacturers the ability to instantly create shelf-stable cannabis-infused beverages. Beverages made this way can resist microbial growth and chemical degradation for a minimum of 3 months.

C. DEFINITIONS

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

As used herein, CBD refers to cannabidiol.

As used herein, $\Delta^9$-THC refers to $\Delta^9$-tetrahydrocannabinol.

As used herein, $\Delta^8$-THC refers to $\Delta^8$-tetrahydrocannabinol.

As used herein, "anti-emetic" refers to compounds capable of reducing nausea, enhancing appetite and/or reducing vomiting in an individual.

As used herein, "effective amount" refers to the administration of an amount of a given compound that achieves the desired effect. For example, regarding the combination of CBD and $\Delta^8$-THC, an "effective amount" is an amount sufficient for or that is capable of reducing nausea or vomiting and/or enhancing appetite in a patient or individual in need of such treatment. The patient may be a human patient.

As used herein, "purified" does not require absolute purity but is instead intended as a relative definition. For example, purification of starting material or natural material to at least one order of magnitude, preferably two or three orders of magnitude, is expressly contemplated as falling within the definition of "purified."

As used herein, the term "isolated" requires that the material be removed from its original environment.

As used herein, the terms "subject" and "patient" are used interchangeably irrespective of whether the subject has or is currently undergoing any form of treatment. As used herein, the terms "subject" and "subjects" may refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgus monkey, chimpanzee, etc.) and a human) The subject may be a human or a non-human. In this context, a "normal," "control," or "reference" subject, patient or population is/are one(s) that exhibit(s) no detectable disease or disorder, respectively.

"Sample," "test sample," and "patient sample" may be used interchangeably herein. The sample can be a sample of serum, urine plasma, amniotic fluid, cerebrospinal fluid, cells (e.g., antibody-producing cells) or tissue. Such a sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. The terms "sample" and "biological sample" as used herein generally refer to a biological material being tested for and/or suspected of containing an analyte of interest such as antibodies. The sample may be any tissue sample from the subject. The sample may comprise protein from the subject.

The terms "determining," "measuring," "assessing," and "assaying" are used interchangeably and include both quantitative and qualitative measurement, and include determining if a characteristic, trait, or feature is present or not. Assessing may be relative or absolute. "Assessing the presence of" a target includes determining the amount of the target present, as well as determining whether it is present or absent.

The term "treating" or "treatment" refers to administration of a compound or agent to a subject who has a disorder or is at risk of developing the disorder with the purpose to cure, alleviate, relieve, remedy, delay the onset of, prevent, or ameliorate the disorder, the symptom of the disorder, the disease state secondary to the disorder, or the predisposition toward the disorder.

The terms "prevent," "preventing," "prevention," "prophylactic treatment," and the like refer to reducing the probability of developing a disorder or condition in a subject (e.g., plant), who does not have, but is at risk of or susceptible to developing a disorder or condition.

The terms "decrease," "reduced," "reduction," "decrease," or "inhibit" are all used herein generally to mean a decrease by a statistically significant amount. However, for avoidance of doubt, "reduced," "reduction" or "decrease" or "inhibit" means a decrease by at least 10% as compared to a reference level, for example, a decrease by at least about 20%, or at least about 30%, or at least about 40%, or at least about 50%, or at least about 60%, or at least about 70%, or at least about 80%, or at least about 90% or up to and including a 100% decrease (e.g., absent level as compared to a reference sample), or any decrease between 10-100% as compared to a reference level.

The word "substantially" does not exclude "completely," e.g., a composition which is "substantially free" from Y may be completely free from Y. Where necessary, the word "substantially" may be omitted from the definition of the invention.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

It is noted here that, as used in this specification and the appended claims, the singular forms "a," "an," and "the" include plural reference unless the context clearly dictates otherwise. The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise.

In cases in which a method comprises a combination of steps, each and every combination or sub-combination of the steps is encompassed within the scope of the disclosure, unless otherwise noted herein.

The section headings as used herein are for organizational purposes only and are not to be construed as limiting the subject matter described.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates, which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

D. EXAMPLES

Example 1

A five-liter round bottom flask is charged with 4.6 kg of CBD and a stir bar. The material is heated to 90 C until and until full stirring is possible. Then 222 grams of aluminum isopropoxide is added and while stirring. The heat is turned off, and the reaction produces its own heat. Once the heat stabilizes, it is increased to 180 C. A sample is taken out every hour to monitor the progress. After 3 hours, 85% of the material is delta 8 and the rest being delta 9, and all the CBD is converted. If the reaction is left too long CBN and delta 10 are formed. The characterization of the products is shown in FIGS. 1 and 2.

Example 2

A five-liter round bottom flask is charged with 4.6 kg of CBD and delta 9 THC and a stir bar. The material is heated to 90° C. until and until full stirring is possible. Then 222 grams of aluminum isopropoxide is added and while stirring. The heat is turned off, and the reaction produces its own heat. Once the heat stabilizes, it is increased to 180 C. A sample is taken out every hour to monitor the progress. After 3 hours, 85% of the material is delta 8 and the rest being delta 9, and all the CBD is converted. If the reaction is left too long CBN and delta 10 are formed.

Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

The yield of the resulting products is between 90-95%, and the purity is above 90%. The yield change depending on the purity of the starting material. Additional distillation, as well as degumming and waxing, may be required when the starting material has low purity. To this end, the material is mixed with ethanol, filtered to remove $Al_2O_3$. Next, ethanol is removed, and the product is distilled to a light yellow and to a colorless oil. If starting with CBD isolate, then it is not required to degum and dewax it again, and only distillation is needed after filtering hot material.

What is claimed is:

1. A method of converting CBD to a tetrahydrocannabinol, comprising:
   (a) providing a reaction mixture comprising a solid catalyst in an organic solvent, wherein the solid catalyst comprises aluminum isopropoxide;
   (b) adding a reagent comprising CBD to the reaction mixture;
   (c) mixing the reaction mixture and allowing a reaction for converting CBD to a tetrahydrocannabinol to occur for a predetermined period of time;
   (d) removing the solid catalyst by filtration upon the completion of the reaction;
   (e) removing the organic solvent; and
   (f) eluting the tetrahydrocannabinol from an organic phase.

2. The method of claim 1, wherein the tetrahydrocannabinol comprises 8-tetrahydrocannabinol (8-THC).

3. The method of claim 2, wherein the tetrahydrocannabinol also comprises 9-tetrahydrocannabinol (9-THC).

4. The method of claim 1, wherein the yield of the tetrahydrocannabinol is at least 60%.

5. The method of claim 1, wherein the yield of the tetrahydrocannabinol is at least 80%.

6. The method of claim 1, wherein the yield of the tetrahydrocannabinol is at least 90%.

7. The method of claim 3, wherein the ratio of 8-THC to 9-THC is between about 1:10 and about 10:1.

8. The method of claim 3, wherein the ratio of 8-THC to 9-THC is between about 1:1 and about 6:1.

9. The method claim 3, wherein the ratio of 8-THC to 9-THC is between about 2:1 and about 5:1.

10. The method of claim 1, following mixing the reaction mixture, heating the reaction mixture to a temperature between about 70° C. and about 110° C. to allow complete mixing.

11. The method of claim 10, comprising, following mixing the reaction mixture, the reaction mixture is heated to about 90° C. to allow complete mixing.

12. The method of claim 10, wherein heating is stopped when the reaction mixture is substantially mixed.

13. The method of claim 1, wherein removing the organic solvent is performed under a pressure near atmospheric pressure to a pressure substantially below atmospheric pressure.

14. The method of claim 1, wherein mixing the reaction mixture is performed under a nitrogen atmosphere.

15. The method of claim 1, comprising eluting the tetrahydrocannabinol on an HPLC column.

16. The method of claim 1, comprising eluting the tetrahydrocannabinol on an RPHPLC column.

17. The method of claim 1, wherein the tetrahydrocannabinol is eluted with water-methanol or water-acetonitrile.

18. The method of claim 1, wherein the reagent further comprises a tetrahydrocannabinol.

19. The method of claim 18, wherein the tetrahydrocannabinol of the reagent is 9-THC.

* * * * *